US008630713B2

(12) United States Patent
Adib (10) Patent No.: US 8,630,713 B2
(45) Date of Patent: Jan. 14, 2014

(54) ELECTRICAL MUSCLE STIMULATOR

(75) Inventor: Fray Adib, Seattle, WA (US)

(73) Assignee: Myotronics-Noromed, Inc., Tukwila, WA (US)

( * ) Notice: Subject to any disclaimer, the term of this patent is extended or adjusted under 35 U.S.C. 154(b) by 1107 days.

(21) Appl. No.: 10/942,622

(22) Filed: Sep. 16, 2004

(65) Prior Publication Data

US 2005/0096711 A1 May 5, 2005

Related U.S. Application Data

(60) Provisional application No. 60/503,397, filed on Sep. 16, 2003.

(51) Int. Cl.
*A61N 1/18* (2006.01)

(52) U.S. Cl.
USPC .......................................................... 607/45

(58) Field of Classification Search
USPC ............................... 607/45–46, 115–116, 118
See application file for complete search history.

(56) References Cited

U.S. PATENT DOCUMENTS

| 3,447,537 | A | * | 6/1969 | King | 607/140 |
| 3,659,614 | A | * | 5/1972 | Jankelson | 607/139 |
| 6,788,975 | B1 | * | 9/2004 | Whitehurst et al. | 607/45 |

* cited by examiner

*Primary Examiner* — Rex R Holmes
(74) *Attorney, Agent, or Firm* — Christensen O'Connor Johnson Kindness PLLC (57) ABSTRACT

Disclosed are a method and apparatus for stimulating the masticatory, shoulder, or back, and facial muscles. This is achieved by way of placing four output electrodes and at least one common electrode in the vicinity of the head, neck, and shoulder or back of a subject. In particular, two output electrodes are placed adjacent to the ears of the subject and two output electrodes are placed along the upper back of the subject. The at least one common transmitting electrode is placed on the back of the neck of the subject, generally just below the hairline. Stimulation of muscles/nerves in the vicinity of each output electrode is achieved substantially simultaneously by way of the current produced by the output electrodes.

18 Claims, 7 Drawing Sheets

ELECTRICAL MUSCLE STIMULATOR

CROSS-REFERENCE TO RELATED APPLICATION

The instant application claims priority benefit under 35 U.S.C. §119(e) of Provisional Application No. 60/503,397, filed Sep. 16, 2003. The entire contents of the provisional application are incorporated herein by reference.

FIELD OF THE INVENTION

The present invention generally relates to electrical muscle stimulators, and more particularly, the present invention generally relates to electrical muscle stimulators designed to stimulate the masticatory and facial muscles, and in addition, various muscles of the shoulder and back.

BACKGROUND OF THE INVENTION

The stimulation of muscles in the human body by way of electrical stimuli to provide involuntary muscular response has become a useful remedial, diagnostic, and clinical technique. One example where electrical stimuli are used to provide involuntary muscular response relates to masticatory and facial muscles. In particular, the muscles that directly relate to the mandibular closure.

Generally, instead of stimulating the actual muscles associated with the mandibular closure, nerves associated with the mandibular and facial muscles are stimulated to attempt to achieve remedial, diagnostic, and clinical results. This is because direct stimulation of the muscles is impractical due to the number of electrodes that would be required to stimulate these muscles. Moreover, electrical stimulation of nerve fibers associated with masticatory and facial muscles helps to ensure stimulation of the entire muscle complex associated with the mandible. Furthermore, six to eight times less electrical energy is required to effectively stimulate the motor nerves than would be required for direct muscle stimulation of the masticatory and facial muscles.

Use of electrical stimulation of the motor nerves controlling the masticatory and facial muscles allows for near balanced closure of the mandible. If simultaneous and bilateral stimulation of the masticatory and facial muscles can be achieved, a number of clinical and diagnostic techniques are possible. For example, controlled stimulation may be employed to diagnose the comparative degree of relaxation or contracture of the muscle groups on each side of the face, to cause the mandible to close to the horizontal myocentric position of the occlusion, to determine the vertical position of occlusion, to make denture impressions, to relax muscle spasms associated with temporomandibular joint syndrome (TMJ), and to reduce post-operative swelling and discoloration by causing gentle massage as the muscles contract.

Furthermore, since pain and spasm associated with mandibular and facial muscles can be referred to shoulder and back muscles, the relaxation and therapy of shoulder and back muscles are of particular importance. To accomplish desired results requires a versatile apparatus adapted to provide amplitude pulses to the nerve fibers that control the masticatory, back and shoulder, and facial muscles. Generally, these amplitude pulses are provided by way of electrical stimulus of particular quantity and duration that provides for near optimum stimulation of the muscles without undue fatigue. For example, an intermittent or a pulsing current having a duration of about half (½) a millisecond and the frequency of about 40 pulses per minute may be used to stimulate the nerves associated with the muscles.

It has been found that the current electrical stimulation devices provide somewhat satisfactory results associated with the masticatory and facial muscles. However, improvements may be made in current techniques used to stimulate the masticatory and facial muscles.

SUMMARY OF THE INVENTION

The exemplary embodiments of the present invention provide a method and apparatus for stimulating the masticatory and facial muscles. This is achieved by way of placing four output electrodes and at least one common electrode in the vicinity of the head of a subject. In particular, two output electrodes are placed adjacent to the ears of the subject and two output electrodes are placed along the upper back of the subject. At least one common electrode is placed on the back of the neck of the subject, generally just below the hairline. Stimulation of muscles/nerves in the vicinity of each output electrode is achieved substantially simultaneously by way of the current pulses produced by the output electrodes.

According to an exemplary embodiment of the present invention a method is provided that includes placing one electrode in the vicinity of each ear of a subject, placing one electrode in the vicinity located on either side of a neck of the subject, and placing at least one electrode along the back of the neck of the subject.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
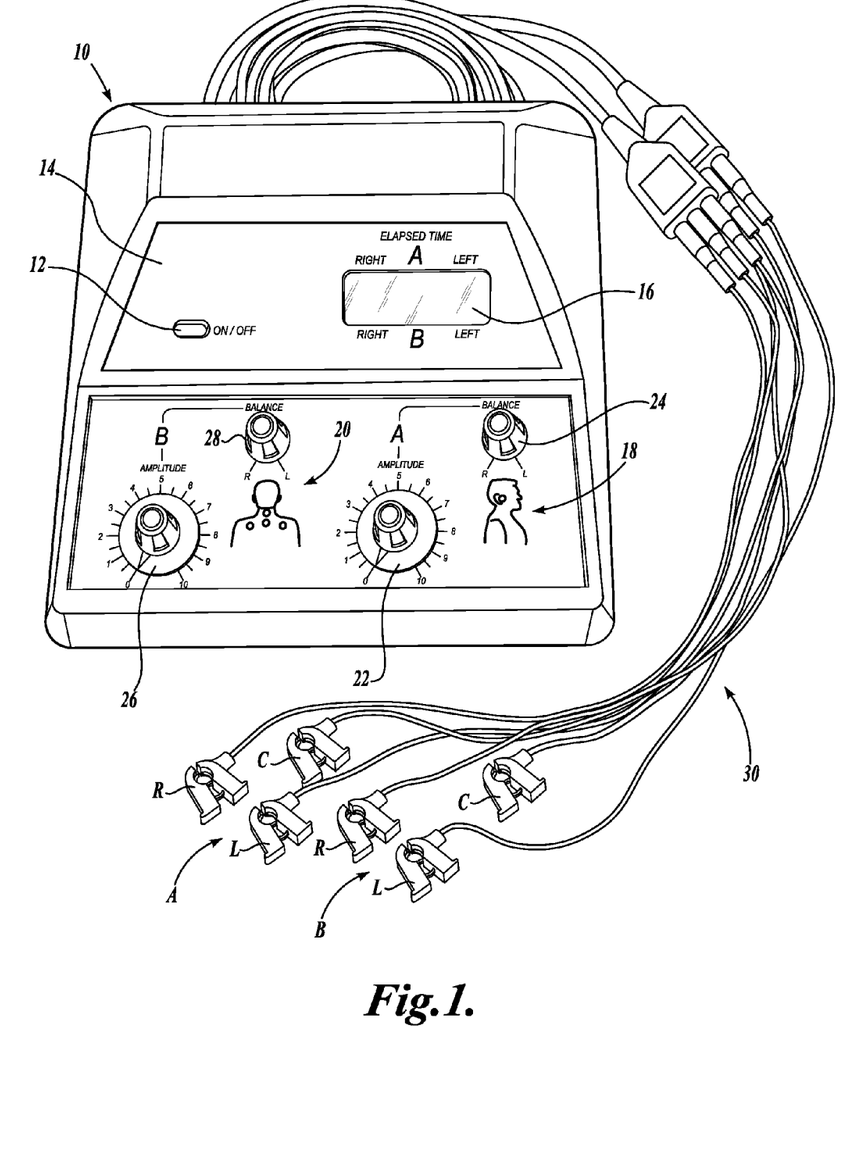
FIG. 1 illustrates a mandible stimulator in accordance with an exemplary embodiment of the present invention.

FIG. 1 illustrates a mandible stimulator 10 in accordance with an exemplary embodiment of the present invention. As is illustrated in the figure, the mandible stimulator 10 includes an on/off switch 12 that is located on a front panel 14. The front panel further includes a display 16 that is designed to show a total elapsed time of the device during use thereof. The display 16 is also capable of showing indicators as to when current is being applied to particular channels of the mandible stimulator 10.

The front display 14 also includes various controls in the lower portion thereof. These controls include an amplitude and balance bank A 18 and an amplitude and balance bank B 20. The amplitude and balance bank A 18 includes an amplitude gain dial 22 and a balance dial 24. Similarly, the amplitude and balance bank B 20 includes an amplitude gain dial 26 along with a balance dial 28.

As is further illustrated in FIG. 1, the mandible stimulator 10 includes cables 30 that may be connected to electrodes (discussed hereinafter). The cables 30 are divided into two distinct groups. One group is associated with the amplitude and balance bank A 18 controls and the other group is associated with the amplitude and balance bank B 20. The division of the cables 30 is illustrated in FIG. 1.

Figure 2:
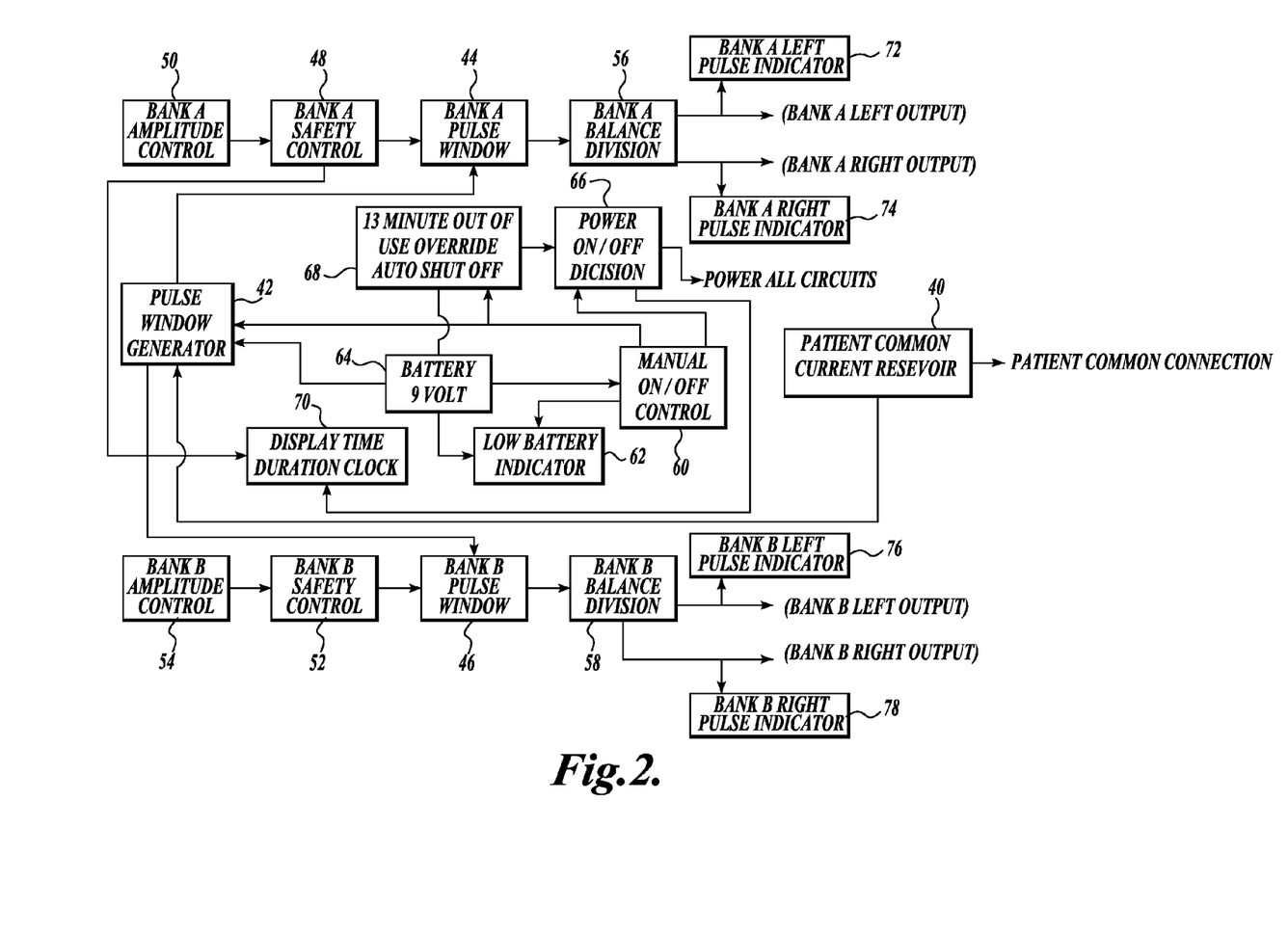
FIG. 2 illustrates a block diagram of the various exemplary elements contained within the mandible stimulator.

FIG. 2 illustrates a block diagram of the various exemplary elements contained within the mandible stimulator 10. As one of ordinary skill in the art will appreciate, the various exemplary elements may be implemented as analog/digital circuitry. As is illustrated in the figure, the mandible stimulator 10 contains a common current reservoir 40 that is generally connected to two of the cables 30. These cables are labeled with a "C" in FIG. 1. The cables detect the presence of current within the body of a subject.

The common current reservoir 40 is operatively connected to a pulse window generator 42. The pulse window generator 42 functions to provide a current timing pulse to a bank A pulse window block 44 and a bank B pulse window block 46. The bank A pulse window block 44 is in communication with a bank A safety override 48 and a bank A amplitude control 50. Similarly, the bank B pulse window block 46 is in communication with a bank B safety override block 52 and a bank B amplitude control block 54. Further in communication with the bank A pulse window block 44 is a bank A balance division block 56. Similarly, the bank B pulse window block 46 is in communication with a bank B balance division block 58. The pulse window generator block 42 in concert with the bank B blocks 46, 52, 54, and 58 provide a pulsed current to the right and left bank B output cables of the cables 30. Moreover, the bank A blocks 44, 48, 50, and 56 in concert with the pulse window generator block 42 provide a pulsed current output via the bank A left and right output cables of the cables 30. The amplitude of the pulsed current may be adjusted using the dials 22 and 26 of the mandible stimulator 10. Moreover, the balance of the supplied pulsed current may be adjusted using the dials 24 and 28.

As is further illustrated in FIG. 2, the device 10 includes a manual power on/off control block that is in communication with an optional low battery indicator block 62 and a battery 64, such as a 9-volt battery. The manual on/off control 60 is further in communication with a power on/off decision block 66. Further illustrated in FIG. 2 is a 13-minute out of use override auto shutoff block 68 along with a display time duration clock block 70. Finally, the block diagram illustrated in FIG. 2 includes bank A left and right pulse indicators 72 and 74 along with bank B left and right pulse indicators 76 and 78. These indicators are shown on the display 16 when current is being applied to the output leads of the cables 30.

Figure 3:
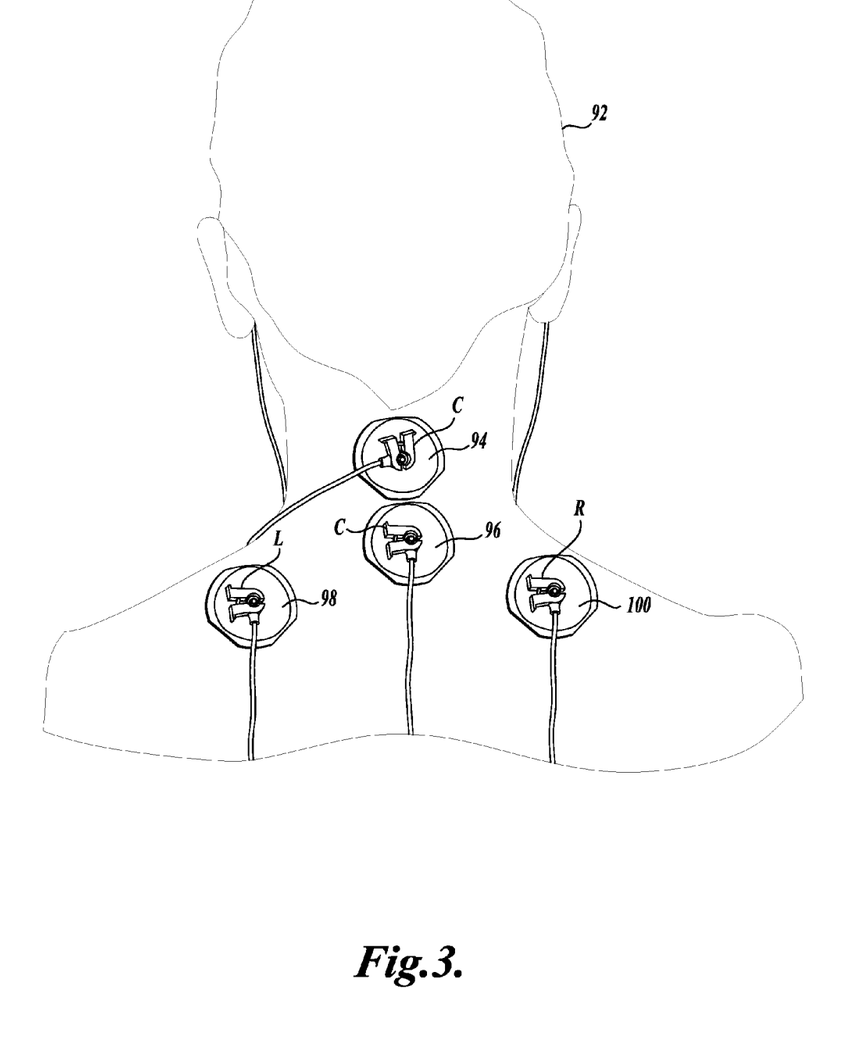
FIGS. 3 and 4 illustrate various electrodes connected to a subject, in accordance with an exemplary embodiment of the present invention.
Figure 4:
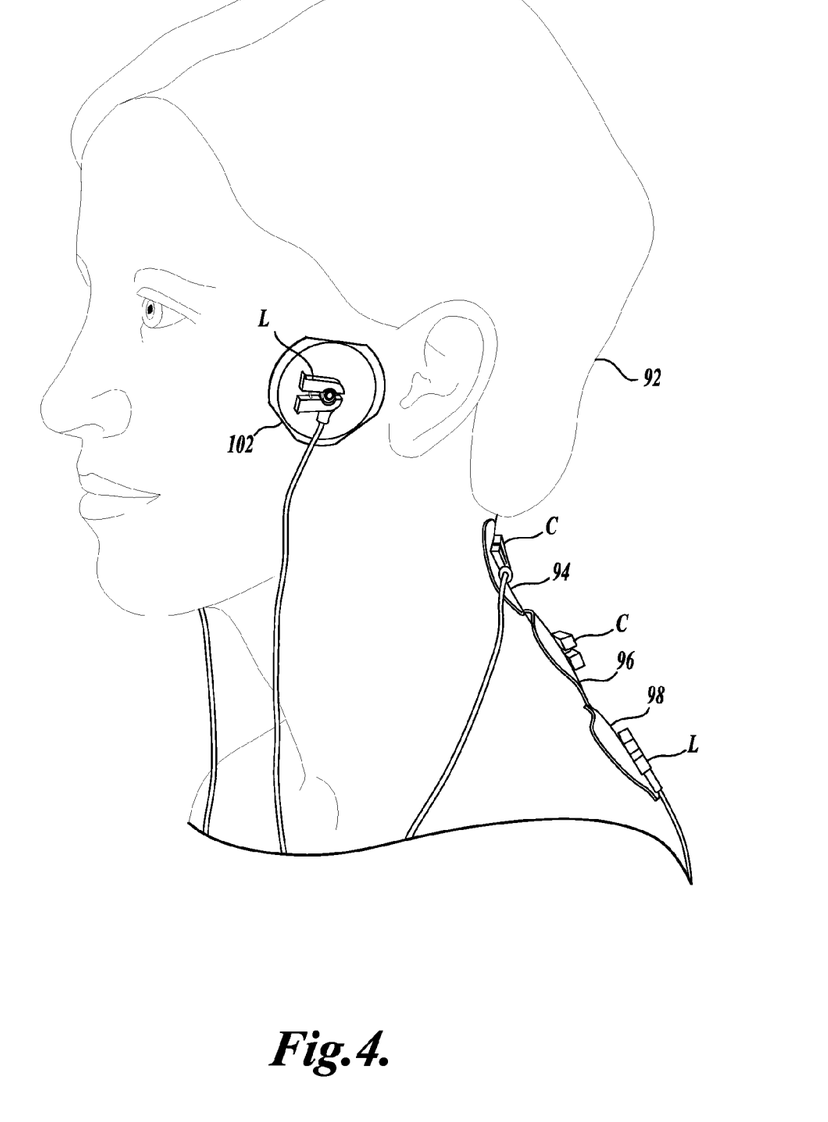

FIGS. 3 and 4 illustrate various electrodes 90 connected to a subject 92. As illustrated in FIG. 3, two electrodes 94 and 96 are connected on a back part of the neck of the subject 92 and positioned substantially below the hairline of the subject 92. Although the two electrodes 94 and 96 are shown as two electrodes, they may also be integrated and implemented as one electrode. Two additional electrodes 98 and 100 are positioned on either side of the electrodes 94 and 96 positioned on the back of the neck. The electrodes 98 and 100 positioned on either side of the electrodes 94 and 96 on the subject's shoulder or back are current producing electrodes, whereas the electrodes 94 and 96 on the subject's neck are non current producing electrodes.

FIG. 4 illustrates a left facial view of the subject 92. As is illustrated in the figure, an additional electrode 102 is placed adjacent to the subject's ear. Also illustrated in FIG. 4 are the electrodes 94, 96, and 98. Another electrode, similar to the electrode 102, is placed adjacent to the ear on the right side of the subject 92. The electrode 102 and the additional electrode adjacent the other ear are current transmitting electrodes.

Figure 5:
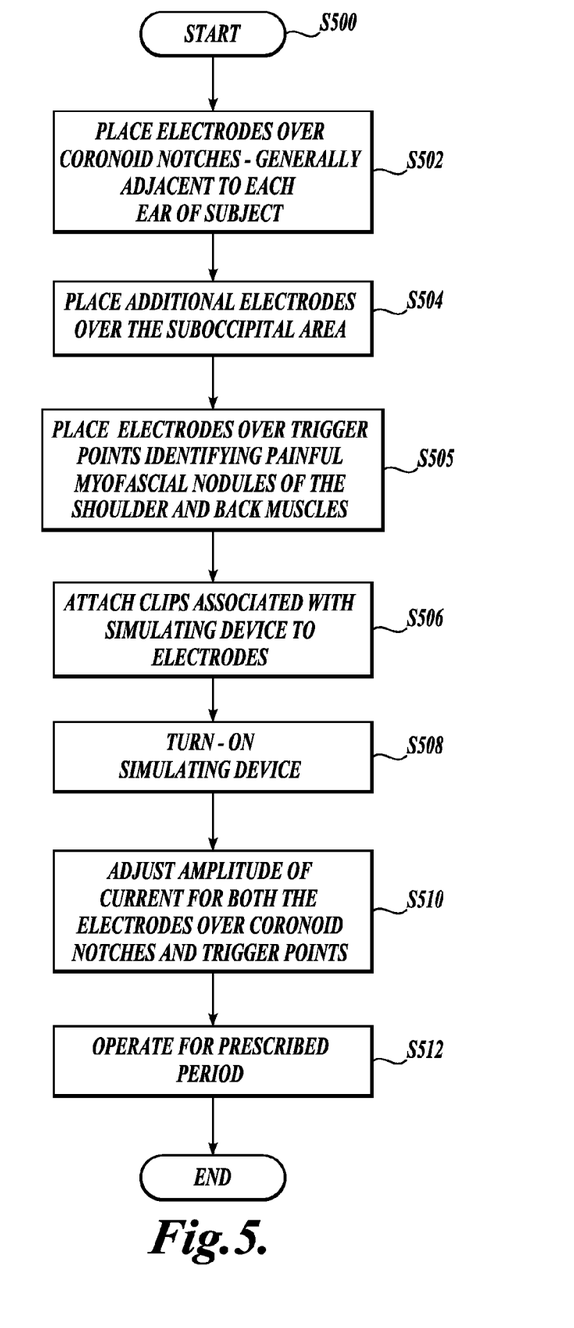
FIG. 5 illustrates a method in accordance with an exemplary embodiment of the present invention.

FIG. 5 illustrates a method in accordance with an exemplary embodiment of the present invention. As is illustrated in FIG. 5, the process of stimulating nerves and/or muscles associated with the subject starts with block 5500. Foremost, current producing electrodes are placed over the coronoid notches of the subject, which are generally adjacent to each ear of the subject (S502). The current may be provided by way of the mandible stimulator 10 and the L and R wires controlled by the bank A controls (FIG. 1).

Next, non current producing electrodes are placed over the suboccipital area (S504). The suboccipital area is generally directly below the hairline of the subject. These electrodes placed below the hairline and on the back neck of the subject are not current producing electrodes. Then, current producing electrodes are placed over trigger points of shoulder or back muscles that identify painful myofascial nodules (S505). The current may be provided by way of the mandible stimulator 10 and the L and R wires controlled by the bank B controls (FIG. 1). Identification of the trigger points may be accomplished by way of massaging the subject to discover potentially painful myofascial nodules. These nodules are generally found in the shoulder and back muscles.

After placement of the electrodes, clips associated with the stimulating device are connected to the placed electrodes. The electrodes placed over the coronoid notches along with the electrodes placed over the myofascial shoulder or back nodules each receive current from the stimulating device 10. However, the electrodes placed over the suboccipital area of the subject do not receive current. These are conducting electrodes that are placed on the suboccipital area.

Following the placement of the electrodes, the stimulating device 10 may be turned on (S508). Once the device is on, the amplitude of the current supplied to the electrodes over the coronoid notches and the trigger points may be adjusted as desired by the practitioner operating the stimulating device 10 (S510). Continued operation of the stimulating device 10 over a prescribed period is at the discretion of the practitioner (S512).

While the preferred embodiment of the invention has been illustrated and described, it will be appreciated that various changes can be made therein without departing from the spirit and scope of the invention.

A first configuration described in applicant's J5 User's Guide as set forth in U.S. Provisional Application No. 60/503, 397 and expressly incorporated by reference herein, uses a total of 6 electrodes, namely, a set of three (3) electrodes for each bank of two (2) channels. The three electrodes in each set consist of one common (active) electrode placed on the neck below the hairline, and two (left and right) passive electrodes. The current is directed from the active electrode to the other two electrodes.

The two active electrode leads are shorted together internally. The two active electrodes are placed adjacent to each other (one below the other) to distribute the current among the two electrodes, providing reduced current density that results in enhanced patient comfort.

All six electrodes used in this configuration can be made of standard electrodes, including Mytotronics' Myotrode II wet gel electrodes.

In a second configuration, a total of 5 electrodes are used. The unique feature in this configuration is the use of one (1) active electrode from which current flows to four (4) sites.

The active electrode is larger than the other four electrodes. The active electrode is 1.6 inches by 1.6 inches in size and uses Myotronics solid gel material that has a superior uniformity of current distribution. In this configuration, only one active lead is used.

As will be appreciated by those of ordinary skill in the art, the present invention is not limited to electrodes of any particular size or shape. Although this illustrative example utilizes electrodes having a size of 1.6 inches by 1.6 inches, the systems and method described herein can use electrodes that have a larger or smaller size.

The Model J-5 Myo-monitor is a low frequency neuromuscular stimulator. It emits an electrical impulse at a fixed rate of once every 1.5 seconds and at an amplitude high enough to elicit muscle contractions. This rhythmic pumping action of the muscles increases blood flow. Muscle spasm is relieved since fresh blood and oxygen are pumped in while accumulated toxins are flushed out.

The Model J-5 has two cables that are connected to the back of the instrument, each cable containing leads related to two stimulating channels. Output to each cable is controlled by its own amplitude and balance controls. The controls are labeled Set "A" (for TMJ/Occlusal stimulation) and Set "B" (for cervical and thoracic stimulation).

The practitioner has the choice of using either cable Set "A" or Set "B" by itself, or both Sets "A" and "B" simultaneously. If using only one cable at a time, it is best to simply disconnect the unused cable.

Figure 6:
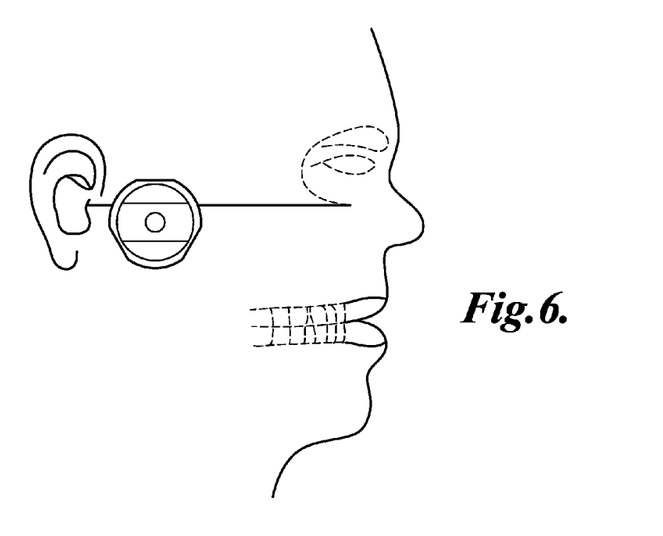
FIGS. 6 and 7 illustrate TMJ/occlusal placement of electrodes according to an embodiment of the invention.
Figure 7:
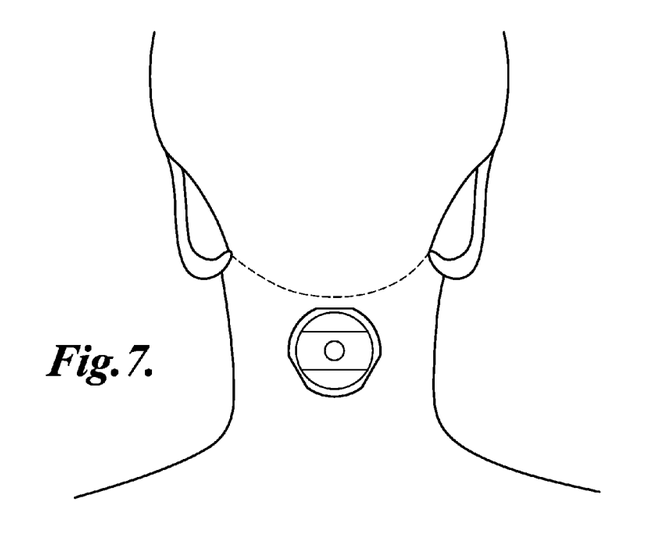
Figure 8:
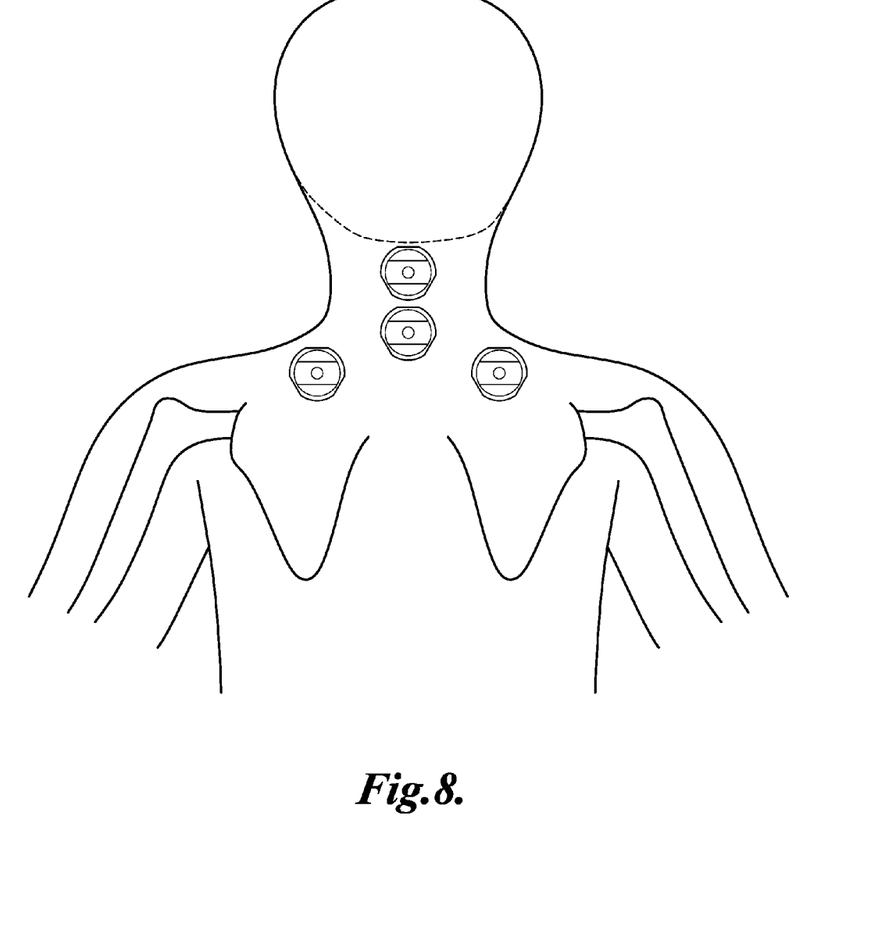
FIG. 8 illustrates cervical placement of electrodes according to an embodiment of the invention.

Skin preparation is the same regardless of which cable set is used. Identify the locations of electrode placement for the area planned to be stimulated as shown in FIGS. 6, 7, and 8. Follow the general instructions for skin preparation and electrode application.

1. Identify Myo-Trode Placement (Myo-trode is a name for high quality disposable stimulating electrodes from Myotronics-Noromed, Inc.)

A. TMJ/Occlusal Placement

Myo-trodes are placed over each coronoid notch (TMJ area) for simultaneous stimulation of the V and VII cranial nerves. These nerves control the muscles of facial expression and mastication. A third Myo-trode (common) is placed at the midline suboccipital area, just below the hairline.

Proper placement of Myo-trodes for this configuration is diagrammed in FIGS. 6 and 7. Care should be taken to properly place the electrodes over the coronoid notch.

B. Cervical Placement

Professionals treating TMJ/MPD recognize that these dysfunctions often have a significant postural component. Triggerpoints may develop as a result of postural over-accommodation. Triggerpoint areas may refer pain to distant sites. Triggerpoints can be found by palpating muscles to identify painful myofascial nodules. The active electrodes should be placed bilaterally over the triggerpoint area where indicated. The third electrode is placed at the midline suboccipital area just below the hairline. A typical placement for upper trapezius spasm relief is diagrammed in FIG. 8. (Note the second common electrode. It is required when stimulating with all four channels simultaneously.)

Caution: Active stimulating electrodes should not be placed over the carotid nerve plexus.

2. Prepare the Skin

A. Study the Myo-trode electrode placement diagrams carefully to identify proper location before proceeding.

B. Scrub the skin thoroughly with alcohol, soap, or water making sure that all cosmetics and skin oils are removed from the area of application and the back of the neck just below the hair line. After scrubbing the area, dry thoroughly.

Note: Long sideburns or profuse hair in the cervical area will not interfere with operation as long as all hair oil has been removed and sufficient gel is used to form a conductive path to the skin.

C. It is especially important to place the Myo-trode III disposable electrode in the correct position.

3. Place Myo-Trodes

Note: Myo-trodes I are recommended for office use. Myo-trodes III are recommended for prescribed home use.

A. Application of the Right and Left Myo-Trodes

1. Holding the tab of the Myo-trode, place according to FIG. 6, 7, or 8. Keep the Myotrode as wrinkle-free as possible.
2. Press the adhesive edges firmly against the skin to assure tight adhesion.
3. In case of long sideburns, brush the hairs of the sideburn forward. This will expose at least one-half inch of bare skin between earlobe and sideburn. After adhering one-half inch of the Myo-trode to the skin, brush sideburn back, smooth the Myo-trode over the exposed sideburn, and adhere it to bare skin in front of the sideburn. In the cervical area, placing electrodes over profuse hair may result in uncomfortable removal of electrode. Shaving the area of application may be considered in this case.

Myo-trode I: Insert Myo-jel by filling a monoject syringe with Myo-jel. Place the open end of the syringe (with plunger removed) over the opening of the Myo-jel bottle. Squeeze gel into syringe until it is half full. Insert plunger back into syringe.

Carefully inject gel into the area under the plastic screen. Press one finger immediately below the bottom of the screen area. This helps to confine the gel to the screen area, particularly where long sideburns are present.

Apply enough Myo-jel so the screen is completely filled, but do not overfill so that gel oozes out of the top or extends beyond screen area into adhesive. Using moderate pressure, rub the outside of the screen area from the bottom up with your fingers to spread Myo-jel evenly under the screen.

Myo-trode III: Press down on the adhesive firmly to achieve good skin contact.

B. Placement of the Rear Myo-Trode

1. With the patient's head in an erect postural position, move the Myo-trode into position over the nape of the neck as shown in FIGS. 6 and 7, just under the hairline.

Note: It is important that the Myo-trode be in the exact center of the occipital area. When stimulating the occlusal/TMD and cervical areas simultaneously (using all four channels) it is necessary to use two rear Myo-trodes, one above the other, immediately below the hairline.

2. Follow the same procedure described in A above for Myo-trode application.

The embodiments of the invention in which an exclusive property or privilege is claimed are defined as follows:

1. A method of electrical muscle stimulation, the method comprising:
    placing a first and a second current-producing electrode in the vicinity of the left and the right ear, respectively, of a subject on the surface of the skin;
    placing a third and a fourth current-producing electrode in a position located bilaterally below the neck over left and right shoulder muscles, respectively, of the subject on the surface of the skin;

placing at least one non-current-producing electrode along the back of the neck of the subject on the surface of the skin; and substantially simultaneously providing current pulses through the first, second, third, and fourth current-producing electrodes to the at least one non-current-producing electrode to stimulate muscles.

2. The method according to claim 1, wherein each electrode placed in the vicinity of each of the ears is placed forward of each respective ear.

3. The method according to claim 2, wherein each electrode placed in the vicinity of each of the ears is placed over each coronoid notch thereby providing stimulation of various cranial nerves.

4. The method according to claim 1, wherein the at least one electrode placed along the back of the neck of the subject is placed in close proximity of the midline suboccipital area that is generally located below the hairline of the subject.

5. The method according to claim 4, wherein the at least one electrode is two electrodes, the two electrodes being placed in close proximity to each other.

6. The method according to claim 4, wherein the at least one electrode is a single electrode.

7. The method according to claim 1, wherein the at least one non-current-producing electrode comprises two non-current-producing electrodes of the same electrical polarity.

8. A method of electrical muscle stimulation, comprising:
placing multiple electrodes on the surface of the skin of a subject, wherein the multiple electrodes comprise a first electrode placed adjacent to an ear on the left side of the subject, a second electrode placed adjacent to an ear on the right side of the subject, a third electrode placed below the neck on the left side of the back of the subject, and a fourth electrode placed below the neck on the right side of the back of the subject;

placing at least one additional electrode on the surface of the skin on the back of the neck of the subject; and providing current pulses that flow substantially simultaneously from the first, second, third, and fourth electrodes to the at least one additional electrode to stimulate muscles of the subject.

9. The method according to claim 8, wherein the first and second electrodes are each placed forward of the respective ear of the subject.

10. The method according to claim 9, wherein the first and second electrodes are each placed over a coronoid notch of the subject to provide stimulation of cranial nerves.

11. The method according to claim 8, wherein the at least one additional electrode placed on the back of the neck of the subject is placed in close proximity of the midline suboccipital area that is generally located below the hairline of the subject.

12. The method according to claim 11, wherein the at least one additional electrode is two electrodes that are placed in close proximity to each other.

13. The method according to claim 11, wherein the at least one additional electrode is a single electrode.

14. The method according to claim 8, wherein the at least one additional electrode comprises two electrodes of the same electrical polarity.

15. The method according to claim 8, wherein the third and fourth electrodes are respectively placed over shoulder muscles on the left and right sides of the back of the subject.

16. A method of electrical stimulation of a subject, comprising:
placing two active electrodes in close proximity to each other on the back of the neck of a subject at a midline suboccipital area;

placing a first set of left and right passive electrodes bilaterally below the neck over the left and right shoulder muscles, respectively, of the subject, wherein a first electrode of the two active electrodes is electrically associated with the first set of left and right passive electrodes;

placing a second set of left and right passive electrodes on the subject near the left and right ears, respectively, of the subject over a coronoid notch, wherein a second electrode of the two active electrodes is electrically associated with the second set of left and right passive electrodes; and substantially simultaneously providing current pulses from the two active electrodes to the first and second sets of left and right passive electrodes to stimulate the subject.

17. The method of claim 16, further comprising separately controlling the amplitude of the current pulses provided respectively from each of the two active electrodes to the first and second sets of passive electrodes.

18. The method of claim 16, further comprising separately controlling the balance of the current pulses provided respectively from each of the two active electrodes to the first and second sets of passive electrodes.

* * * * *